(12) United States Patent
Sanso'

(10) Patent No.: US 11,406,658 B2
(45) Date of Patent: Aug. 9, 2022

(54) COMPOSITION COMPRISING GLYCYRRHIZIN AND COSMETIC AND PHARMACEUTICAL USES THEREOF

(71) Applicant: ATG 20 S.R.L., Pisa (IT)

(72) Inventor: Marco Aldo Sanso', Pisa (IT)

(73) Assignee: ATG 20 S.R.L., Pisa (IT)

( * ) Notice: Subject to any disclaimer, the term of this patent is extended or adjusted under 35 U.S.C. 154(b) by 0 days.

(21) Appl. No.: 17/259,403

(22) PCT Filed: Jul. 15, 2019

(86) PCT No.: PCT/IB2019/056003
§ 371 (c)(1),
(2) Date: Jan. 11, 2021

(87) PCT Pub. No.: WO2020/016732
PCT Pub. Date: Jan. 23, 2020

(65) Prior Publication Data
US 2021/0121497 A1   Apr. 29, 2021

(30) Foreign Application Priority Data
Jul. 18, 2018 (IT) .................. 102018000007291

(51) Int. Cl.
| | |
|---|---|
| *A61K 31/728* | (2006.01) |
| *A61K 31/704* | (2006.01) |
| *A61K 47/36* | (2006.01) |
| *A61K 47/38* | (2006.01) |
| *A61K 47/32* | (2006.01) |
| *A61K 47/46* | (2006.01) |
| *A61K 47/12* | (2006.01) |
| *A61K 47/02* | (2006.01) |
| *A61K 9/00* | (2006.01) |
| *A61K 9/08* | (2006.01) |
| *A61K 47/26* | (2006.01) |

(52) U.S. Cl.
CPC .......... *A61K 31/728* (2013.01); *A61K 9/0048* (2013.01); *A61K 9/08* (2013.01); *A61K 31/704* (2013.01); *A61K 47/02* (2013.01); *A61K 47/12* (2013.01); *A61K 47/26* (2013.01); *A61K 47/32* (2013.01); *A61K 47/36* (2013.01); *A61K 47/38* (2013.01); *A61K 47/46* (2013.01)

(58) Field of Classification Search
CPC ...... A61K 31/728; A61K 47/36; A61K 47/38; A61K 8/602; A61K 8/73; A61K 8/731; A61K 9/0014; A61Q 19/00; A61Q 19/005
See application file for complete search history.

(56) References Cited

U.S. PATENT DOCUMENTS

| | | |
|---|---|---|
| 8,501,822 B2 | 8/2013 | Matsumoto et al. |
| 2010/0279981 A1* | 11/2010 | Del Prete ............... A61P 27/04 514/54 |

FOREIGN PATENT DOCUMENTS

| | | |
|---|---|---|
| CN | 106560218 A | 4/2017 |
| EP | 2444058 A1 | 4/2012 |
| JP | 2000344656 A | 12/2000 |
| JP | 2013067580 A | 4/2013 |
| JP | 2015010070 A | 1/2015 |
| JP | 2015010071 A | 1/2015 |
| JP | 2016098185 A | 5/2016 |
| WO | 2010044261 A1 | 4/2010 |
| WO | 2018066651 A1 | 4/2018 |

OTHER PUBLICATIONS

Search Report and Written Opinion of PCT/IB2019/056003 dated Oct. 21, 2019.

* cited by examiner

*Primary Examiner* — Anna R Falkowitz (74) *Attorney, Agent, or Firm* — Silvia Salvadori, P.C.; Silvia Salvadori (57) ABSTRACT

The invention discloses a composition comprising glycyrrhizin, hyaluronic acid or a salt or a derivative thereof, and a viscosizing agent. The composition therefore finds advantageous application in all those cosmetic and therapeutic indications in which glycyrrhizin is used, since the composition according to the invention significantly improves the bioavailability thereof.

20 Claims, 3 Drawing Sheets

COMPOSITION COMPRISING GLYCYRRHIZIN AND COSMETIC AND PHARMACEUTICAL USES THEREOF

This application is a U.S. national stage of PCT/IB2019/056003 filed on 15 Jul. 2019, which claims priority to and the benefit of Italian Application No. 102018000007291 filed on 18 Dec. 2018, the contents of which are incorporated herein by reference in their entireties.

FIELD OF THE INVENTION

The present invention relates to a composition comprising glycyrrhizin, hyaluronic acid and a viscosizing agent. The composition therefore finds advantageous application in all those cosmetic and therapeutic indications in which glycyrrhizin is used, since the composition according to the invention significantly improves the bioavailability thereof.

BACKGROUND ART

Glycyrrhizin (or glycyrrhizic acid or glycyrrhizinic acid) is a triterpenoid saponin glycoside which constitutes the active ingredient of liquorice extract:

Glycyrrhizin is also available in the form of salts, such as dipotassium glycyrrhizate (or dipotassium glycyrrhizinate) and (mono) ammonium glycyrrhizate (or (mono) ammonium glycyrrhizinate or GA). In acidic form, it is not particularly water-soluble, but potassium salt is, however, water-soluble:

while (mono)ammonium salt is soluble in diluted acidic or basic solutions:

When glycyrrhizin is hydrolyzed, the resultant aglycone is the 18β-glycyrrhetinic acid (or glycyrrhetic acid), also known as enoxolone:

In the field of food, glycyrrhizin is employed as a sweetener, since it is up to 50 times sweeter than saccharose and, in comparison with the latter, the sweet flavour is perceived later but lasts longer in the mouth.

In the pharmacological field, this compound is used as an expectorant and as a gastroprotective agent in case of peptic ulcers.

Glycyrrhizin has, furthermore, an anti-inflammatory and antiphlogistic action; indeed, it has been highlighted that glycyrrhetic acid inhibits the conversion of cortisol into cortisone by 11 beta hydroxysteroid dehydrogenase and inhibits the production of inflammatory cytokines such as TNF-α and IL-1β. (Xiaoying Huang et al. *Anti-Inflammatory Effects of Monoammonium Glycyrrhizinate on Lipopolysaccharide-Induced Acute Lung Injury in Mice through Regulating Nuclear Factor-Kappa B Signaling Pathway. EvidBasedComplementAlternatMed.* 2015; 2015: 272474.)

Recently, a further mechanism has been identified, which is responsible for the antiphlogistic action of this drug, namely the capacity of glycyrrhizin to inhibit the production of free radicals, which are a class of powerful inflammatory agents, by neutrophils. The molecule appears, however, to be incapable of significantly influencing phagocytosis and chemotaxis of these cells.

It is interesting to note that the free radicals produced by the leucocytes are one of the main causes of damage to the follicular epithelium in the event of acne and rosacea. Furthermore, this compound is used clinically for the treatment of chronic hepatitis and allergic disorders. A glycyrrhizin injection is administered to patients with chronic hepatitis C and long-term use thereof is effective in preventing the development of hepatocellular carcinoma. Repeated painful endovenous injections reduced, however, the quality of life for patients with chronic hepatitis. Injection therapy also involves the risk of infections for healthcare workers. Oral administration has therefore been employed but the bioavailability of glycyrrhizin has proved to be extremely low.

Literature provides accounts of various attempts to improve the bioavailability of glycyrrhizin; for example Sasaki et al. (*Improvement in the bioavailability of poorly absorbed glycyrrhizin via various non-vascular administration routes in rats*, Int J Pharm. 2003 Oct. 20; 265(1-2):95-102) compared various routes for the administration of glycyrrhizin, concluding that the nasal route and the rectal route, especially in the presence of fatty acid salts, such as topical permeation promoters, were better than the oral route.

Nevertheless, these routes of administration are somewhat uncomfortable for the patients and in any case not suitable in the event that localised treatments, whether internal or external, are necessary.

The object according to the present invention is therefore to increase the bioavailability of glycyrrhizin, in particular when administered by external topical route.

SUMMARY OF THE INVENTION

Said object has been achieved by a composition comprising glycyrrhizin, hyaluronic acid or a salt or a derivative thereof, and a viscosizing agent selected from tamarind seed polysaccharide, PVP, carboxyvinyl polymers, xanthan gum, carboxymethylcellulose (CMC), hydroxyethyl cellulose (HEC), hydroxypropyl methylcellulose (HPMC), mucopolysaccharides, cellulose and esters thereof, natural gums and esters thereof, pectins, polyacrylates, and mixtures thereof, as stated in claim 1.

For the purposes of the present invention, the term "glycyrrhizin" is meant to include glycyrrhizic acid, the salts thereof, preferably potassium and ammonium salts, the hydrolyzed forms thereof, preferably glycyrrhetic acid, and mixtures thereof.

In another aspect, the present invention concerns the use of said composition in the treatment of ocular affections.

In a further aspect, the present invention concerns an ophthalmic product comprising said composition.

In another aspect, the present invention concerns the use of said composition in the topical treatment of dermatological, gynecological, otorhinolaryngological or dental pathologies.

In a still further aspect, the present invention concerns the cosmetic use of said composition, in particular as a soothing agent in products for external topical use.

BRIEF DESCRIPTION OF THE FIGURES

The characteristics and advantages of the present invention will become clear in the following detailed description of the embodiments provided by way of non-limiting examples and illustrated in the drawings annexed hereto, in which.

DETAILED DESCRIPTION OF THE INVENTION

The invention therefore relates to a composition comprising glycyrrhizin, hyaluronic acid or a salt or a derivative thereof, and a viscosizing agent selected from tamarind seed polysaccharide, PVP, carboxyvinyl polymers, xanthan gum, carboxymethylcellulose, hydroxyethyl cellulose, hydroxypropyl methylcellulose, mucopolysaccharides, cellulose and esters, natural gums and their esters, pectins, polyacrylates, and their mixtures.

Preferably, the glycyrrhizin is in a concentration of up to 5.0 wt %, based on the weight of the composition.

More preferably, the glycyrrhizin is in a concentration of 0.05-3.0 wt %, based on the weight of the composition.

With the term "hyaluronic acid salt", it is meant sodium hyaluronate, potassium hyaluronate, iron hyaluronate, calcium hyaluronate, magnesium hyaluronate, zinc hyaluronate, cobalt hyaluronate, ammonium hyaluronate, tetrabutylammonium hyaluronate, or a mixture thereof.

The term "hyaluronic acid derivative" is meant to comprise:

hyaluronic acid esters, wherein a part or all the carboxylic groups are esterified with aliphatic, aromatic, arylaliphatic, cycloaliphatic, heterocyclic series alcohols, as also described in EP0216453B1, self-cross-linked hyaluronic acid esters, wherein a part or all of the carboxylic groups are esterified with alcoholic groups from the same polysaccharide chain or further chains, as also described in EP0341745B1, cross-linked hyaluronic acid compounds, wherein a part or all of the carboxylic groups are esterified with aliphatic, aromatic, arylaliphatic, cycloaliphatic, or heterocyclic series polyalcohols, generating cross-linking by means of spacer chains, as also described in EP0265116B1, succinic acid hemiesters or succinic acid heavy metal salts with hyaluronic acid or with partial or total hyaluronic acid esters, as also described in WO96/357207, O-sulfated derivatives, as also described in WO95/25751, or N-sulfated derivatives, as also described WO/1998/045335, and mixtures thereof.

Preferably, the weight average molecular weight of said hyaluronic acid or a salt or a derivative thereof is 200-1500 kDa, more preferably 600-1000 kDa.

Preferably, said hyaluronic acid or a salt or a derivative thereof is in a concentration of up to 5.0 wt %, based on the weight of the composition.

More preferably, said hyaluronic acid or a salt or a derivative thereof is in a concentration of 0.01-3.0 wt %, based on the weight of the composition.

In preferred embodiments, the composition comprises hyaluronic acid.

In particularly preferred embodiments, the hyaluronic acid is in a concentration of 0.1-2.0 wt %, based on the weight of the composition.

The term "tamarind seed polysaccharide" means the polysaccharide moiety obtainable from the seeds of *Tamarindus indica*, also referred to hereinafter for the sake of brevity as "TSP" (from the English term "*Tamarindus indica* Seed Polysaccharide").

As it is known, the tamarind tree is common in India, in Africa, and throughout the Far East, where it is grown essentially for food purposes. The seed, which was originally a by-product, has since found various uses, sometimes ground up into a mealy product (currently known as "raw tamarind gum or "tamarind nut powder"), above all in the textile and paper industry, where it is used respectively as a sizing agent for yarn and as a gluing agent, and in the food industry, where it is used as a thickener, gelling agent, stabiliser and binder in all kinds of products, much the same ways as further polysaccharide products, such as alginates, pectins, the guar gum or the locust bean meal. Raw tamarind gum (commercially available, for example, as Glyloid® produced by Dai-nippon Pharmaceutical Co. LTD based in Osaka, Japan) typically contains, in addition to 65-73 wt % polysaccharide, also 15-23% protein material, 3-8% oils and fats and 2-4% ash, as well as traces of raw fibre, tannins, and further impurities.

One advantageous aspect is that the TSP solutions are suitable to be sterilized by a passage in autoclave (for example for 20 minutes at 120° C.) without undergoing thermal degradation, unlike as occurs, for example, with hyaluronic acid. The possibility of sterilization by simply a passage in autoclave renders the TSP-based preparations particularly convenient from a production viewpoint.

Furthermore, TSP has demonstrated significant mucomimetic, mucoadhesive, and bioadhesive properties.

TSP is a purified, neutral, water-soluble polysaccharide fraction comprising a polymeric molecule of galactoxyloglucan which is very hydrophilic and features a ramified structure: attached to the main linear chain, formed of glucose repeating units, are small monosaccharide units of xylose and disaccharide units of xylose-galactose, in the latter case, the galactose is at the end of the side chain. The three monomers are present in a molar ratio of 3:1:2 and constitute approximately 65% of the components of the seed:

As can be observed, the "mucin-like" molecular structure determines the excellent mucoadhesive properties of the polysaccharide, derived from the formation of bonds, of various kinds, with said mucins.

TSP can be isolated by means of chemical methods and enzymatic methods, using protease or a combination of protease and high intensity ultrasounds. In the chemical method, 20 g Tamarind seed powder are added to 200 ml cold distilled water to prepare a suspension which is then poured into 800 ml boiling distilled water. The solution thus formed is left to boil for 20 minutes and stirred continually; after resting for one night, said solution, undergoes centrifugation at 5000 rpm for 20 minutes. The supernatant is separated and poured into a volume of pure alcohol amounting to double the amount of said supernatant. Thus, a precipitate is obtained which is then washed with pure ethanol and air-dried. Finally, the dried polymer is ground up, sieved, and stored in a dryer until use. In the enzymatic method, the powder obtained from the seeds is mixed with ethanol and then treated with protease; subsequently, said powder is centrifuged and ethanol is added to the supernatant for precipitation. Finally, the polymer is separated and dried.

Preferably, the weight average molecular weight of the TSP is 450-750 kDa.

Preferably, said viscosizing agent is in a concentration of up to 5.0 wt %, based on the weight of the composition.

More preferably, said viscosizing agent is in a concentration of 0.01-3.0 wt %, based on the weight of the composition.

In preferred embodiments, said viscosizing agent is TSP, CMC, or a mixture thereof, more preferably in a concentration of 0.05-2.0 wt %, based on the weight of the composition.

In more preferable embodiments, said viscosizing agent comprises TSP, preferably in a concentration of 0.05-2.0 wt %, based on the weight of the composition. Alternatively, said viscosizing agent comprises a mixture of TSP with one or more of the following: PVP, carboxyvinyl polymers, xanthan gum, carboxymethylcellulose, hydroxyethyl cellulose, hydroxypropyl methylcellulose, mucopolysaccharides, cellulose and esters thereof, natural gums and esters thereof, pectins, and polyacrylates.

Particularly preferred are the compositions wherein said viscosizing agent is TSP, preferably in a concentration of 0.05-2.0 wt %, based on the weight of the composition. Preferably, glycyrrhizin and hyaluronic acid or a salt or a derivative thereof are in a weight ratio of 1:1 to 1:20, more preferably 1:1 to 1:10.

In preferred embodiments, glycyrrhizin and hyaluronic acid or a salt or a derivative thereof are in a weight ratio of 1:1 to 1:5.

Preferably, glycyrrhizin and viscosizing agent are in a weight ratio of 5:1 to 1:15, more preferably 3:1 to 1:10.

In preferred embodiments, glycyrrhizin and viscosizing agent are in a weight ratio of 2:1 to 1:5.

Preferably, hyaluronic acid or a salt or a derivative thereof and viscosizing agent are in a weight ratio of 1:2 to 10:1, more preferably 1:1 to 5:1.

In preferred embodiments, hyaluronic acid or a salt or a derivative thereof and viscosizing agent are in a weight ratio of 1:1 to 3:1.

Preferably, the composition of the invention has a pH of 4-7.

More preferably, the composition of the invention has a pH of 5.5-6.5.

In preferred embodiments, the composition of the invention comprises a buffer which serves to maintain the selected pH.

Preferably, the buffer is in a concentration of up to 5 wt %, based on the weight of the composition.

More preferably, the buffer is in a concentration of 2.0-4.0 wt %, based on the weight of the composition.

In particularly preferred embodiments, the buffer is in a concentration of 1.5-2.5 wt %, based on the weight of the composition.

Preferably, said buffer is selected from citric acid-sodium citrate, acetic acid-sodium acetate, boric-sodium borate acid, citric acid-disodium hydrogen phosphate (also known as 'McIlvaine buffer'), citric acid-monopotassium phosphate-boric acid-diethylbarbituric acid, TRIS-borate, and mixtures thereof.

In preferred embodiments, the buffer is citric acid-sodium citrate.

In particularly preferred embodiments, the pH is approximately 6 and the buffer is citric acid-sodium citrate.

In further embodiments, the composition of the invention features a conductibility of 0.1-2.0 mS/cm, measured at 25° C., preferably 0.2-1.5 mS/cm. As will be seen in the following examples, it was observed that the higher the conductibility, the higher the depolimerizing action of the hyaluronidase, whereas the lower the conductibility, the lower the depolimerizing action of the hyaluronidase. This means that, depending on requirements, conductibility may be modulated towards values near the lower limit of the range stated above for applications such as cosmetics, galenic products, medical devices or pharmaceuticals, for which it is necessary to limit the dosage of the products, or towards values near the upper limit for applications in which frequent use of cosmetic or pharmaceutical preparations is necessary.

When the composition of the invention comprises a buffer, the conductibility can be modulated by varying the weight ratio between the acid compound and the saline compound contained therein. For example, when the buffer is citric acid-sodium citrate, the weight ratio between citric acid and sodium citrate is varied: by increasing the quantity of citric acid, conductibility is reduced; by increasing the quantity of sodium citrate, conductibility is increased.

In further preferred embodiments of the composition of the invention, the water is the only solvent present therein.

In further preferred embodiments, the composition of the invention does not comprise preservatives or colorants.

Preferred compositions have a pH of 4-7 and comprise:
up to 5.0 wt % glycyrrhizin,
up to 5.0 wt % hyaluronic acid or a salt or a derivative thereof,
up to 5.0 wt % viscosizing agent, and
water,
based on the weight of the composition.

More preferable are compositions having a pH of 5.5-6.5 and comprising:
0.05-3.0 wt % glycyrrhizin,
0.01-3.0 wt % hyaluronic acid or a salt or a derivative thereof,
0.01-3.0 wt % viscosizing agent,
up to 5 wt % buffer, and
water,
based on the weight of the composition.

Still more preferable are compositions having a pH of 5.5-6.5 and comprising:
0.05-3.0 wt % glycyrrhizin,
0.01-3.0 wt % hyaluronic acid,
0.01-3.0 wt % TSP, CMC, or a mixture thereof,
2.0-4.0 wt % buffer citric acid-sodium citrate, and
water,
based on the weight of the composition.

Even more preferable are compositions having a pH of pH 5.5-6.5 and comprising:
0.05-3.0 wt % glycyrrhizin,
0.01-3.0 wt % hyaluronic acid,
0.01-3.0 wt % TSP,
2.0-4.0 wt % buffer citric acid-sodium citrate, and
water,
based on the weight of the composition.

In some embodiments, the composition of the invention consists essentially of glycyrrhizin, hyaluronic acid, or a salt or a derivative thereof, and a viscosizing agent selected from tamarind seed polysaccharide, PVP, carboxyvinyl polymers, xanthan gum, carboxymethylcellulose, hydroxyethyl cellulose, hydroxypropyl methylcellulose, mucopolysaccharides, cellulose and esters, natural gums and their esters, pectins, polyacrylates, and their mixtures. The expression "consists essentially of" means that the three components listed above are the only active ingredients present in the composition of the invention, while any further components or excipients do not interfere with the action thereof, and are water-miscible and water-soluble.

In further embodiments, the composition of the invention consists of glycyrrhizin, hyaluronic acid or a salt or a derivative thereof, and a viscosizing agent selected from tamarind seed polysaccharide, PVP, carboxyvinyl polymers, xanthan gum, carboxymethylcellulose, hydroxyethyl cellulose, hydroxypropyl methylcellulose, mucopolysaccharides, cellulose and esters, natural gums and their esters, pectins, polyacrylates, and their mixtures.

The composition of the present invention can be prepared by using commonly known methods. Indeed, the components can, for example, be mixed as such or with one or more excipients, added one after another, under stirring.

In some embodiments, the compositions of the present invention are sterilized before use, according to commonly known methods, for example, under treatment with gamma rays. In another aspect, the present invention concerns the use of said composition in the treatment of ocular affections.

The term "ocular affection" means an inflammatory condition affecting the surface of the eye, such as dry eye syndrome, Sjögren syndrome, uveitis, conjunctivitis, keratitis, keratoconjunctivitis, vernal keratoconjunctivitis, corneal ulcer, atopic keratoconjunctivitis, cicatrising conjunctivitis, blepharitis, keratitis, lagophthalmos, endophthalmitis, episcleritis and scleritis.

In a still further aspect, the present invention concerns an ophthalmic product comprising said composition.

Said ophthalmic product can be a tear substitute, collyrium, a suspension, an eye spray, a foam, a wet wipe, a spray-on patch, or a combination thereof.

In preferred embodiments, said ophthalmic product is a tear substitute.

As will be seen in the examples provided below, the composition of the invention offers a number of advantages not only from a physical-chemical and rheological viewpoint, but overall from the point of view of the effectiveness derived from the synergy of its components. Indeed, firstly, the composition of the invention increases the bioavailability of glycyrrhizin, and secondly, the concomitant presence of glycyrrhizin and viscosizing agent inhibits the effect of hyaluronidase, an enzyme which is normally present on the eye's surface and which degrades hyaluronic acid, thus increasing permanence and effectiveness of the latter, consequently reducing the need to perform repeated administrations of the product.

In preferred embodiments of the ophthalmic product comprising the composition of the invention, the viscosizing agent is TSP, CMC or a mixture thereof, more preferably in a concentration of 0.05-2.0 wt %, based on the weight of the composition.

In more preferable embodiments, said viscosizing agent comprises TSP, preferably in a concentration of 0.05-2.0 wt %, based on the weight of the composition.

Alternatively, said viscosizing agent comprises a mixture of TSP with one or more of the following: PVP, carboxyvinyl polymers, xanthan gum, carboxymethylcellulose, hydroxyethyl cellulose, hydroxypropyl methylcellulose, mucopolysaccharides, cellulose and esters thereof, natural gums and esters thereof, pectins, and polyacrylates.

Particularly preferred are the compositions wherein said viscosizing agent is TSP, preferably in a concentration of 0.05-2.0 wt %, based on the weight of the composition. The ophthalmic product according to the invention, also in a unit dose form, can further comprise ophthalmologically acceptable excipients. The term "ophthalmologically acceptable excipient" means a compound or a mixture suitable for use in a composition for the administration to the external surface of the eye. For example, an excipient of this kind generally shall not cause an adverse reaction in the user, nor significantly inhibit, the action of the actives on the eye's surface.

Suitable excipients are antioxidants, gelling agents, sequestrants, binders, lubricants, thickening agent, tonicity regulators, filmogenic substances, and mixtures thereof.

Accordingly, suitable antioxidants are sodium metabisulphite, sodium thiosulphate, ascorbic acid, sodium ascorbate, glucose, cysteine, and mixtures thereof.

Suitable sequestrants are EDTA and the monosodium, disodium, and potassium salts thereof, diethylene triamine penta methylene phosphonic acid, hexamethylene diamine tetramethyl phosphonic acid, ethylene diamine tetramethyl phosphonic acid, amino trimethylene phosphonates and mixtures thereof.

Preferably, the sequestrants are EDTA, the monosodium, disodium, and potassium salts thereof, and mixtures thereof.

Suitable tonicity regulators are inorganic salts, such as sodium chloride, potassium chloride, magnesium chloride, and calcium chloride, or polyols or sugars, such as glycerol, propylene glycol, erythritol, mannitol, sorbitol, and trehalose, or amino acids, such as carnitine and betaine.

In a further aspect, the present invention concerns the use of said composition in the topical treatment of dermatological, gynecological, otorhinolaryngological or dental pathologies.

In a still further aspect, the present invention concerns the cosmetic use of said composition, in particular as a soothing agent in products for external topical use.

The glycyrrhizin contained in the composition of the invention can indeed be useful in products intended for the treatment and protection of sensitive and delicate skins, since it is effective as a soothing agent, for example, in formulations for children, in aftershaves and in after-sun products, in products for skin which is inflamed, reddened, or prone to atopic and seborrheic dermatitis and irritations in general. It performs its activity even in small doses (between 0.5 and 1%), at which level it does not have any side effects. Therefore, it renders obsolete the use of liquorice extracts which contain low percentages of 18β-glycyrrhetic acid and which can lend the end product an unattractive dark colour.

When the pharmaceutical or cosmetic composition is to be administered by external or internal topical route, said composition is preferably in the form of a solution, lotion, emulsion, suspension, gel, ointment, cream, paste, solution spray, transdermal patch, spray-on patch, foam, or wet wipe, wherein the composition is preferably a suspension or is dissolved in one or more suitable excipients.

Examples of excipients which are suitable for these forms of administration are mineral oil, liquid paraffin, white Vaseline, propylene glycol, polyoxyethylene, polyoxypropylene, emulsifying wax, stearyl alcohol, isostearyl alcohol, cetylstearyl alcohol, stearic acid, glyceryl stearate, sodium lauryl sarcosinate, glycerine, diethylene glycol monoethyl ether, polyethylene glycols, polyethylene glycol stearates, starch, carbopol, carbomers, methyl paraben, Poloxamer 407, Macrogol 400, purified bentonite, propyl paraben, myristyl propionate, dimethicone, titanium dioxide, anionic, cationic and non-ionic surfactants, water, and mixtures thereof.

Preferably the pharmaceutical or cosmetic composition according to the invention is to be administered by topical external route.

It should be also understood that all the combinations of preferred aspects of the components of the composition, as well as of the products containing the same, their preparation and uses, as above reported, are to be deemed as hereby disclosed, and similarly preferred.

It should also be also understood that all combinations of the preferred aspects of the composition of the invention, preparation processes, and uses disclosed above are to be understood as herein described.

Below are working examples of the present invention provided for illustrative purposes.

EXAMPLES

Materials

| Compound | Manufacturer | Abbreviation | Physical state |
|---|---|---|---|
| Hyaluronic acid | Altergon HD | HAS | Powder |
| Tamarind extract | Indena Group | TSP | Powder |
| Ammonium glycyrrhizinate | Indena Group | GA or Glyc. | Powder |
| Carboxymethylcellulose | Ashland | CMC | Powder |
| Monohydrate citric acid | Sigma Aldrich | Citric ac. | Powder |
| Tribasic sodium citrate dihydrate | Sigma Aldrich | Sodium citrate | Powder |
| Mannitol | Sigma Aldrich | — | Powder |
| Water deionised by means of Culligan deionizing system | — | $d\text{-}H_2O$ | Liquid |
| Deuterated water with deuteration degree of 99.9% | Cortecnet | $D_2O$ | Liquid |
| Sodium nitrate | Sigma Aldrich | $NaNO_3$ | Powder |
| Sodium Azide | Sigma Aldrich | $NaN_3$ | Powder |
| I-S type bovine testicular hyaluronidase, enzymatic units 400-1000 units/mg solid | Sigma Aldrich | Hya | Powder |

Preparation of Compositions Comprising HAS, TSP, and GA

Compositions were prepared in $d\text{-}H_2O$ and in citrate buffer with a final content (given as a weight/volume percentage) amounting to 0.4% HAS and 0.2% TSP; the GA, meanwhile, was added in different concentrations (0.05%, 0.1%, and 0.2% weight/volume).

Step 1: approximately 400 mg HAS were dissolved in 30 ml $d\text{-}H_2O$ in a 100 ml flask, then left under stirring at room temperature for 24 h, to ensure the complete dissolution thereof.

Step 2: the components of the citrate buffer (2.8 g mannitol, 0.8 g sodium citrate, 0.01 g citric acid) were weighed and dissolved in 30 ml $d\text{-}H_2O$ at room temperature; after which 200 mg TSP was added under magnetic stirring, maintaining the same temperature. Upon complete dissolution, at Step 2, Step 1 was added. For the compositions in $H_2O$, the 200 mg TSP were dissolved in $d\text{-}H_2O$ only.

Step 3: a stock solution was prepared with 2% weight/volume of GA, by weighing approximately 400 mg into a 50 ml round-bottomed flask, which was subsequently dissolved warm (50° C. by means of an oil bath) in 20 ml $d\text{-}H_2O$; once the solution had cooled, the following samples were taken, which were subsequently added to Step 2:

10 ml for the compositions with 0.2% GA;
5 ml for the compositions with 0.1% GA;
2.5 ml for the compositions with 0.05% GA.

After the additions, the compositions were brought up to volume (100 ml) in $d\text{-}H_2O$ and, at the end of the preparation was the pH measured, obtaining approximately 6.5 for the compositions in the citrate buffer and approximately 5 for those in water.

Example 1: Composition of HAS, TSP and 0.1% GA in Citrate Buffer

Step 1: 0.4003 g HAS were weighed and dissolved in 30 ml $d\text{-}H_2O$ at room temperature.
Step 2: the components of the citrate buffer were weighed (2.8003 g mannitol, 0.8002 g sodium citrate, 0.0103 g citric acid) and dissolved in 30 ml $d\text{-}H_2O$ at room temperature; after which 0.2004 g TSP was added and, upon complete dissolution Step 1 was added. Step 3: 0.4004 g GA were weighed and dissolved in 20 ml $d\text{-}H_2O$ by heating to a temperature of 50° C. by means of an oil bath.

Upon complete solubilization, and after leaving the stock solution to cool, 5 ml Step 3 was added to Step 2.

Finally, the solution was brought up to volume (100 ml) in $d\text{-}H_2O$. Final pH: 6.97

Example 2: Composition of HAS, TSP and 0.1% GA in Water

Step 1: 0.4005 g HAS were weighed and dissolved in 30 ml $d\text{-}H_2O$ at room temperature.
Step 2: 0.2002 g TSP were weighed and dissolved in 30 ml $d\text{-}H_2O$ at room temperature. Upon complete dissolution, Step 1 was added.
Step 3: 0.4002 g GA were weighed and dissolved in 20 ml $H_2O$ by heating to a temperature of 50° C. by means of an oil bath.

Upon complete solubilization, and after leaving the stock solution to cool, 5 ml Step 3 was added to Step 2. Finally, the solution was brought up to volume (100 ml) in $d\text{-}H_2O$. Final pH: 5.70

Preparation of Compositions Comprising HAS, CMC, and GA

Compositions were prepared in $d\text{-}H_2O$ and in citrate buffer with a final content, (given as a weight/volume percentage), amounting to 0.4% HAS and 0.2% CMC; the GA, meanwhile, was added in different concentrations (0.05%, 0.1% and 0.2% weight/volume).

Step 1: approximately 400 mg HAS were dissolved in 30 ml $d\text{-}H_2O$ in a 100 ml flask, then left under stirring at room temperature for 24 h, to ensure complete dissolution thereof.

Step 2: the components of the citrate buffer were weighed (2.8 g mannitol, 0.8 g sodium citrate, 0.01 g citric acid) and dissolved in $d\text{-}H_2O$; after which were added, under magnetic stirring and at room temperature, 200 mg CMC. Upon complete dissolution, Step 1 was added to Step 2. For the compositions in $H_2O$, the 200 mg CMC were dissolved in $d\text{-}H_2O$ only.

Step 3: a stock solution was prepared with 2% weight/volume of GA, by weighing approximately 400 mg into a 50 ml round-bottomed flask, which was subsequently dissolved warm (50° C. by means of an oil bath) in 20 ml $d\text{-}H_2O$; once the solution had cooled, the following samples were taken, which were subsequently added to Step 2:

10 ml for the compositions with 0.2% GA;
5 ml for the compositions with 0.1% GA;
2.5 ml for the compositions with 0.05% GA.

After the additions, the compositions were brought up to volume (100 ml) in $d\text{-}H_2O$. At the end of the preparation the pH was measured, obtaining approximately 6.5 for the compositions in citrate buffer and approximately 5 for those in water.

Example 3: Composition HAS, CMC and 0.1% GA in Citrate Buffer

Step 1: 0.4007 g HAS were weighed and dissolved in 30 ml $d\text{-}H_2O$ at room temperature.
Step 2: the components of the citrate buffer were weighed (2.8001 g mannitol, 0.8008 g sodium citrate, 0.0107 g citric acid) and dissolved at room temperature in 30 ml $d\text{-}H_2O$. After which, 0.2004 g CMC was added and, upon complete dissolution, Step 1 was added.

Step 3: 0.4004 g GA were weighed and dissolved in 20 ml d-H$_2$O by heating to a temperature of 50° C. by means of an oil bath.

Upon complete solubilization, and after leaving the stock solution to cool, 5 ml Step 3 was added to Step 2. Finally, the solution was brought up to volume (100 ml) in d-H$_2$O. Final pH: 6.63

Example 4: Composition of HAS, CMC, and 0.1% GA in Water

Step 1: 0.4006 g HAS were weighed and dissolved in 30 ml d-H$_2$O at room temperature.

Step 2: 0.2009 g CMC were weighed and dissolved in 30 ml d-H$_2$O at room temperature. Upon complete dissolution, Step 1 was added.

Step 3: 0.4004 g GA were weighed and dissolved in 20 ml d-H$_2$O by heating to a temperature of 50° C. by means of an oil bath.

Upon complete solubilization, and after leaving the stock solution to cool, 5 ml Step 2 was added to Step 1. Finally, the solution was brought up to volume (100 ml) in d-H$_2$O. Final pH: 5.05

Buffer Modification Assessment

Compositions were prepared in which the concentration of sodium citrate was modified, with a final content (given as a weight/volume percentage) amounting to 0.4% HAS and 0.2% TSP; the GA, meanwhile, was added in different concentrations (0.05%, 0.1%, and 0.2% weight/volume).

Step 1: approximately 400 mg HAS were dissolved in 30 ml d-H$_2$O in a 100 ml flask, then left under stirring at room temperature for 24 h, to ensure the complete dissolution thereof.

Step 2: the components of the citrate buffer were weighed (2.8 g mannitol, 0.2 g sodium citrate, 0.01 g citric acid) and dissolved in d-H$_2$O; after which were added, under magnetic stirring and at room temperature, 200 mg TSP. Upon complete dissolution, to Step 2 was added the Step 1. For the compositions in H$_2$O, the 200 mg TSP were dissolved in sola d-H$_2$O.

Step 3: a stock solution was prepared with 2% weight/volume of GA, by weighing approximately 400 mg into a 50 ml round-bottomed flask, which was subsequently dissolved warm (50° C. by means of an oil bath) in 20 ml d-H$_2$O; once the solution had cooled, the following samples were taken, which were subsequently added to Step 2:

10 ml for the compositions with 0.2% GA;
5 ml for the compositions with 0.1% GA;
2.5 ml for the compositions with 0.05% GA.

After the additions, the compositions were brought up to volume (100 ml) in d-H$_2$O. At the end of the preparation, the pH was measured, obtaining approximately 6.5 for the compositions in citrate buffer and approximately 5 for those in water.

Example 5: Composition of HAS, TSP and 0.1% GA in Modified Citrate Buffer

Step 1: 0.4004 g HAS were weighed and dissolved in 30 ml d-H$_2$O at room temperature.

Step 2: the components of the citrate buffer were weighed (2.8009 g mannitol, 0.2009 g tribasic sodium citrate, 0.0108 g citric acid) and dissolved in 30 ml d-H$_2$O at room temperature. After which, 0.2007 g TSP was added and, upon complete dissolution, Step 1 was added.

Step 3: 0.4004 g GA were weighed and dissolved in 20 ml d-H$_2$O by heating to a temperature of 50° C. by means of an oil bath.

Upon complete solubilization, and after leaving the stock solution to cool, 5 ml Step 3 was added to Step 2. Finally, the solution was brought up to volume (100 ml) in d-H$_2$O. Final pH: 6.02

Characterization:

Size-Exclusion Chromatography

The characterization of the distribution of the molecular weights of HAS, TSP, GA, CMC, of the compositions, and—lastly—of the products of enzymatic digestion, was performed by means of size-exclusion chromatography in conjunction with a multi-detector system under the following chromatographic conditions:

- Instrument: OmniSEC System (Malvern Panalytical Instruments, UK);
  - Detector: refraction index, light scattering (90° and 7°) and viscosimeter;
  - Columns: 2 columns TSKGMPWXL in series (7 mm ID×30 cm L, 13 μm particle size);
  - Mobile phase: NaNO$_3$ 0.1 M+NaN$_3$ 0.05%;
  - Temperature: 40° C.;
  - Flow: 0.6 ml/min;
    - Volume of injection: 100 μl;
    - Duration of chromatographic passage: 60 min;

data was acquired and processed using OmniSEC v 10.31 software and setting the following dn/dc values: 0.155 for the HAS, 0.164 for the TSP, 0.16 for the CMC and 0.159 for the compositions.

The instrument was calibrated with a standard a molecular weight, and known polydispersion and intrinsic viscosity (PolyCAL-Pul57k, MalvernPanalytical Instruments, UK).

Preparation of Sample:

The HAS, TSP, and CMC samples were weighed and dissolved in mobile phase in concentrations of, respectively, approximately 4 mg/ml, 2 mg/ml, and 2 mg/ml; before the injection, approximately 0.5 mg/ml was diluted in mobile phase. The compositions and the products of enzymatic digestion were diluted in mobile phase to a final concentration of between 0.8 and 0.6 mg/ml.

Conductibility, Dynamic Light Scattering (DLS), and Zeta Potential

The size measurements (Rh, nm), and surface load measurements (Zeta Potential, Zp, mV) of HAS, TSP, GA, CMC, and of the compositions were taken with a Zetasizer (MalvernPanalytical) under the following instrumental conditions: Size measurements)

- Vehicle: mannitol 0.15 (Temperature: 25.0° C.; RI 1.334; Viscosity: 0.9639 mPA*s) and mannitol 0.015 (Temperature: 25.0° C.; RI 1.330; Viscosity: 0.8975 mPA*s))
- Temperature: 25° C.
- Disposable polystyrene cuvette, with minimum volume of 1 ml)
- Measurement angle: 173° C. backscatter (NIBS default)
- Number of measurements: 5
- Software: Zetasizer software v 7.12

Measurements of Zeta Potential
- Vehicle: mannitol 0.15 (Temperature: 25.0° C.; RI 1.334; Viscosity: 0.9639 mPA*s; Dielectric constant: 78.5) and mannitol 0.015 (Temperature: 25.0° C.; RI 1.330; Viscosity: 0.8975 mPA*s; Dielectric constant: 78.5)
- Measurement model: Smoluchowski (F(ka) value: 1.50)
- Temperature: 25° C.

- Disposable cuvette for measurement of Zeta potential, compatible with the diffusion barrier method and with MPT-2 autotitrator
- Number of measurements: 5
- Software: Zetasizer software 7.12

Preparation Samples:

The compositions were analyzed in the unaltered state and diluted to 1:10 in deionized water. The samples of HAS, TSP, and CMC were weighed and dissolved in citrate buffer, obtaining a concentration of approximately 4 mg/ml, 2 mg/ml, and 2 mg/ml, and left under stirring for 2 hours for analysis of the compositions in the unaltered state and then the compositions diluted to 1:10 in $H_2O$.

Nuclear Magnetic Resonance (Nmr)

$^1$H-NMR

The $^1$H-NMR spectra of the solution were measured with an Avance spectrometer, operating at 500 MHz ($^1$H) and equipped with a 5 mm Cryo Probe TCI, under the following conditions:
- Pulse sequence: zgcppr
- Temperature: 300° K
- Number of scans: 16
- Recycle time (D1): 12 sec
- Pulse angle (P1): 90° C.
- Solvent: $D_2O$
- Automatic Abs
- Instrumental reference: TSP calibrated to 0 ppm
- Size for the Fourier transform: 132 K
- Processing software: Bruker TOPSPIN 4.02

All the spectra were processed with the EM function (exponential function) and with LB 0.3 Hz for the reduction of background noise.

T1-NMR

The $^1$H-NMR spectra for the calculation of the T1 were acquired with a spectrometer operating at 500 MHz ($^1$H) under the following conditions:
- Pulse sequence: cpmg (Carr-Purcell-Meiboom-Gill)
- Temperature: 300° K
- Number of scans: 20
- Recycle time (D1): 30 sec
- Echo time ($D_2O$): 2 msec
- Pulse angles (P1): 90° and 180°
- Solvent: $D_2O$
- Instrumental reference: TSP calibrated to 0 ppm For the reprocessing of the data the Bruker TOPSPIN 4.02 was used as software, with T1T2 calculation routine or with the dynamic centre.

T2-NMR

The $^1$H-NMR spectra for the calculation of the T2 were acquired with a spectrometer operating at 500 MHz ($^1$H) equipped with a 5 mm Cryo Probe TCI and with a spectrometer operating at 500 MHz ($^1$H) under the following conditions:
- Pulse sequence: T1IR
- Temperature: 300° K
- Number of scans: 10)
- Recycle time (D1): 30 sec
- Pulse angle (P1): 180°
- Solvent: $D_2O$
- Instrumental reference: TSP calibrated to 0 ppm For the reprocessing of the data, the Bruker TOPSPIN 4.02 was used as software, with T1T2 calculation routine or with the dynamic centre.

Preparation Samples for the $^1$H, T1 and T2 Spectra:

4 mg (HAS) and 2 mg (TSP and CMC) were weighed and dissolved in 1 ml $D_2O$ or in 1 ml citrate buffer; subsequently, the sample was lyophilized and dissolve once again in 1 ml $D_2O$. A 4 mg/ml GA stock solution was then prepared and was diluted in both $D_2O$ and in buffer, obtaining concentrations of 2 mg/ml, 1 mg/ml, and 0.5 mg/ml. For the preparation of the samples of the compositions, 1 ml was taken from each sample, subsequently lyophilized and dissolved in 1 ml $D_2O$.

Finally, 0.6 ml was taken from each sample, then transferred to a 5 mm NMR tube.

Results:

Size-Exclusion Chromatography

| Sample | Mw (kDa) | Mn (kDa) | Mw/Mn | [h] (dl/g) | Rh (nm) |
|---|---|---|---|---|---|
| HAS | ~750 | ~600 | ~1.3 | ~14 | ~55 |
| TSP | ~700 | ~500 | ~1.5 | ~6 | ~40 |
| CMC | ~220 | ~62 | ~3.6 | ~6 | ~25 |
| HAS + TSP | ~730 | ~500 | ~1.5 | ~12 | ~50 |
| HAS + CMC | ~600 | ~190 | ~3.0 | ~12 | ~46 |
| HAS + TSP + GA 0.05% | ~700 | ~490 | ~1.5 | ~12 | ~50 |
| HAS + TSP + GA 0.1% | ~700 | ~500 | ~1.5 | ~12 | ~50 |
| HAS + TSP + GA 0.2% | ~750 | ~500 | ~1.5 | ~12 | ~50 |
| HAS + CMC + GA 0.1% | ~570 | ~190 | ~3.0 | ~12 | ~44 |

As can be seen from the chromatographic data shown above, the presence of GA, in the concentrations used in the experimentation, does not alter the chemical-physical properties, such as the molecular weight and viscosity, of either the HAS+TSP complex or the HAS+CMC complex.

Dynamic Light Scattering (DLS) and Zeta Potential

| Sample | Z-Average (nm) | Zp (mV) |
|---|---|---|
| HAS | 51 | −32 |
| TSP | 46 | −5 |
| HAS + TSP | 50 | −16 |
| HAS + CMC | | |
| HAS + TSP + GA 0.05% | 52 | −18 |
| HAS + TSP + GA 0.1% | 43 | −21 |
| HAS + TSP + GA 0.2% | 41 | −22 |

From the data shown above, it can be seen that the presence of GA significantly alters the conformation of the polymer matrix with respect to the compositions with just HAS and TSP: as the concentration of GA increases, both the hydrodynamic radius and the surface load decrease.

Nuclear Magnetic Resonance (NMR)

$^1$NMR Results:

It was observed that, in concentrations above 0-05%, GA has a spectrum which is more compatible with a gel than with a solution.

In the presence of HAS (0.4%) and TSP (0.2%), the NMR profile of the GA changes, which suggests that the two polysaccharides render the dispersion thereof easier, above all in water, and preferably in concentrations above 0.05%.

Figure 1:
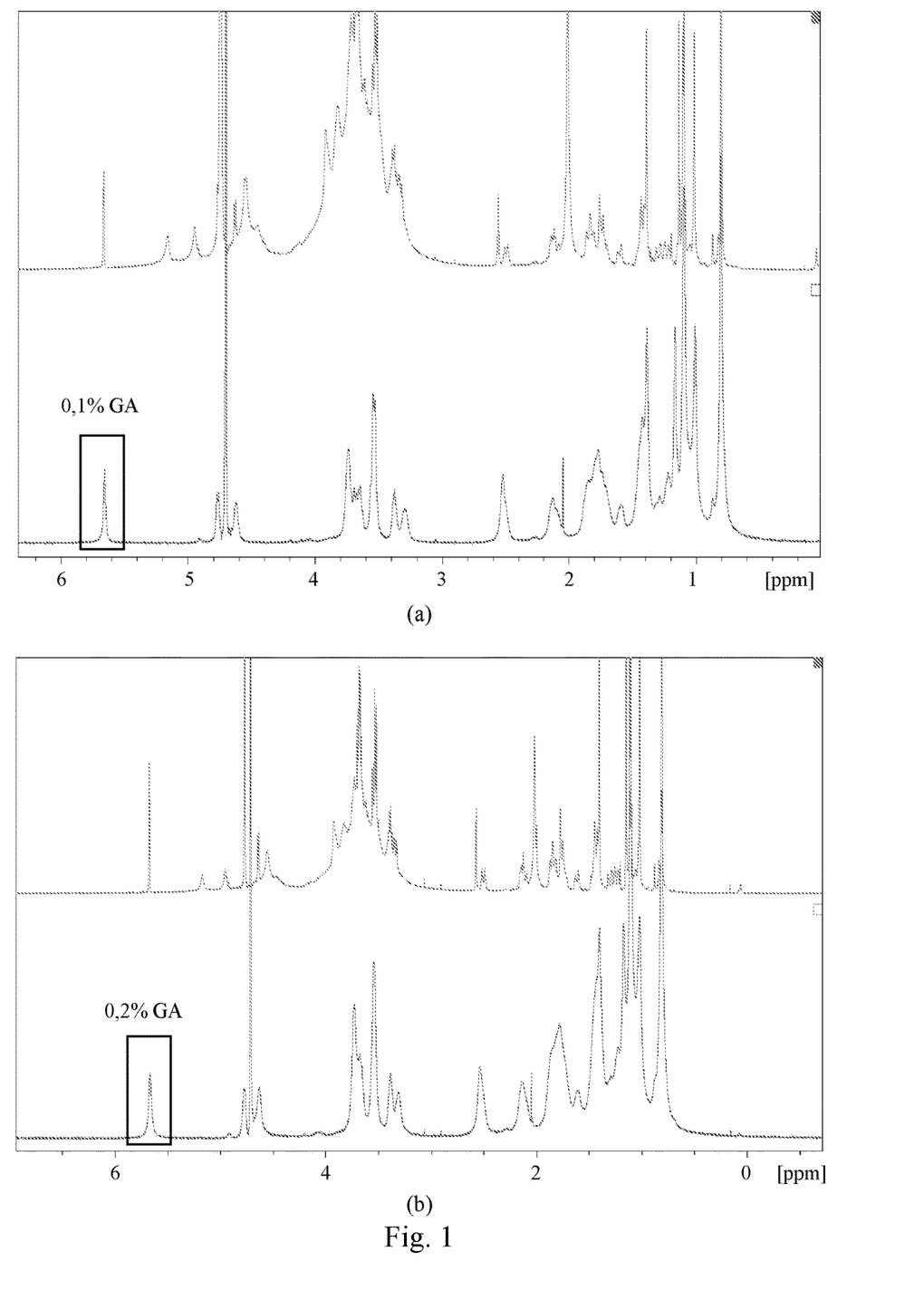
FIG. 1 shows the $^1$NMR spectrum of the composition comprising 0.1% GA (a) and the $^1$NMR spectrum of the composition comprising 0.2% GA (b) in comparison with the $^1$NMR spectrum of GA in the unaltered state.

NMR has also proved to be good analytic approach for the characterization and the quantification of the formulation. Indeed, as can be seen in FIG. 1, a broadening of the GA signal can be observed upon changing from the 0.1% concentration (a) to the 0.2% concentration (b), which was attributed to a greater solubility and dissolution of the molecule in solution in presence of HAS and TSP.

Figure 2:
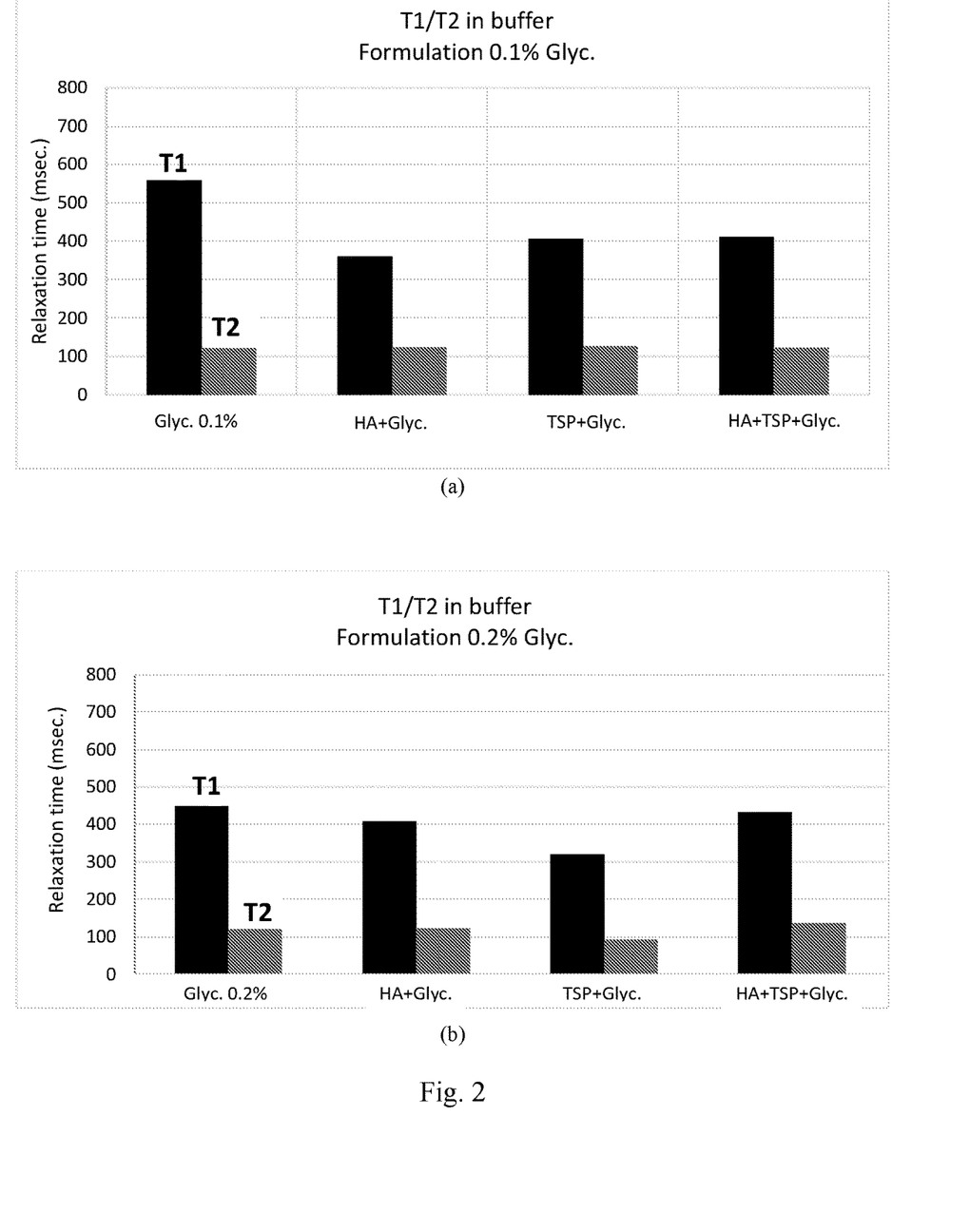
FIG. 2 shows the comparison between the relaxation times T1 and T2 $^1$NMR of the compositions comprising 0.1% GA (a) and 0.2% GA (b), in water.
Figure 3:
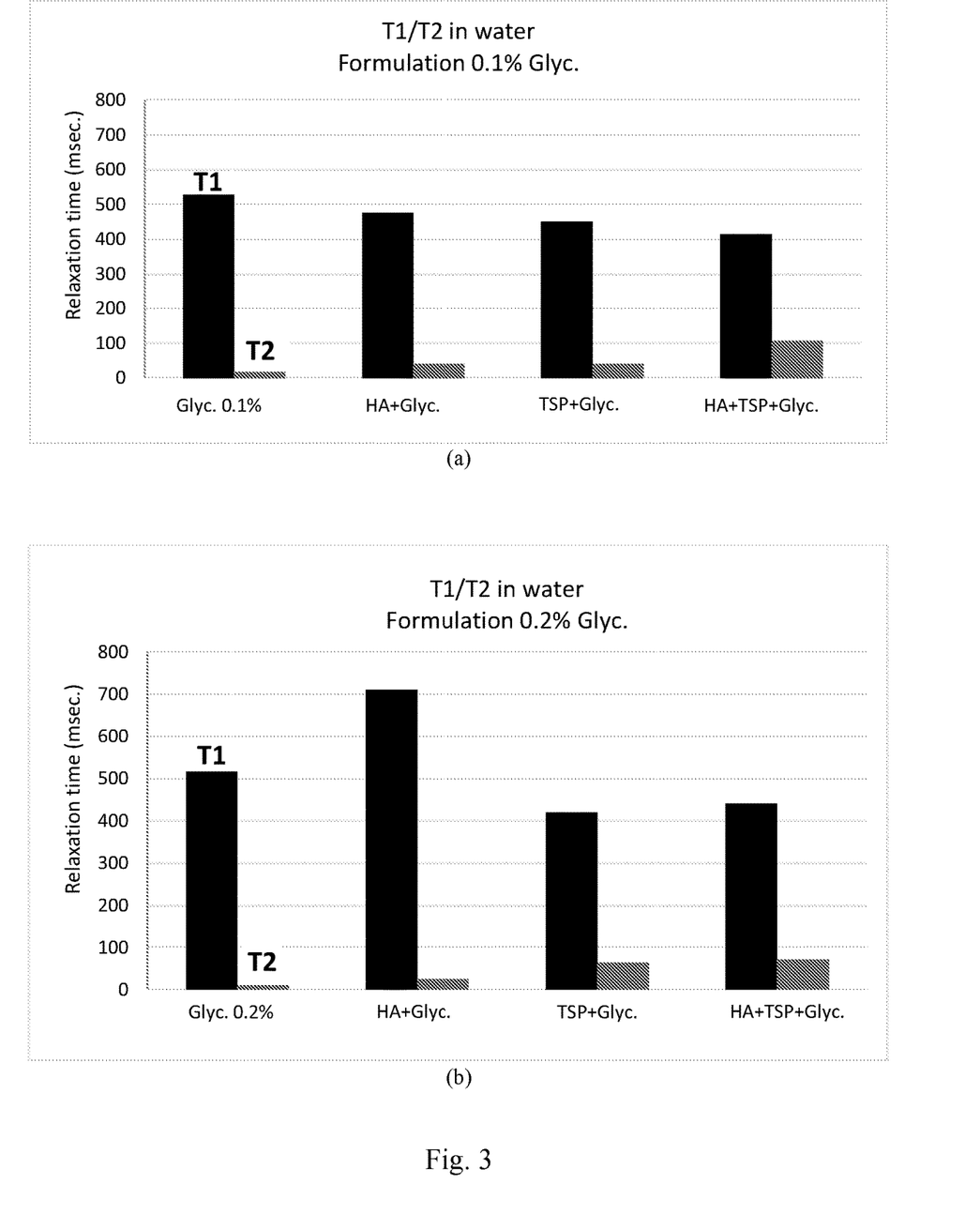
FIG. 3 shows the comparison between the relaxation times T1 and T2 $^1$NMR of the compositions comprising 0.1% GA (a) and 0.2% GA (b), in citrate buffer.

T1 and T2 Results:

With reference to FIGS. 2 and 3, in the presence of HAS (0.4%) and TSP (0.2%), it was observed that:

1) the mean T2 of the GA signals increased in both water and citrate buffer, with the addition of just HAS or just TSP, obtaining greater values in the HAS+TSP mixture. This increase was ascribed to a greater mobility of the of GA molecule and a better dispersion in the solution in the presence of HAS+TSP.
2) In water (FIG. 2), T2 values greater than T1 values indicate a speed which is more compatible with the behaviour of a gel than of a liquid.
3) In water (FIG. 2), the mean T1 values of the GA signal in the formulations HAS+TSP+GA are less than the GA in the unaltered state. This result confirms behaviour compatible with the speed of the movements of solids/gels rather than solutions.
4) In citrate buffer (FIG. 3), the mean T1 and T2 values of the GA signals are comparable, in the different formulations, with the GA in the unaltered state.
5) The values of T2 in buffer (FIG. 3) are greater of the values of T2 in water (FIG. 2) indicating better dispersion of the GA molecules upon changes in the ionic force.
6) In the buffer (FIG. 3), the differences found in water (FIG. 2) are less significant.

Enzymatic Digestion

Enzymatic digestion tests were performed on compositions in both d-$H_2O$ and citrate buffer, prepared following the methods described earlier.

20 mg Hya were weighed and dissolved in 2 ml water at room temperature; 0.1 ml was then taken and added to 50 ml samples of the composition (HAS/Hya ratio by weight amounting to 10/0.1). Digestion was carried out at 38° C. for a period of 24 hours, monitoring the reduction in molecular weight by taking 1 ml samples at 15 and 30 minutes, then every hour for the first 6 h and once after 24 hours). After each sampling, the enzyme was denatured, leaving the sampled solution at 100° C. under stirring for 5 minutes and then filtered to remove the enzyme precipitate (filters: LLG-Syringe filter, CA pore size 0.20 μm, Ø 13 mm).

Calculation of the decrease, as a percentage, in molecular weight over time:

$$\frac{Mw_{t0} - Mw_{tn}}{Mw_{t0}} \times 100$$

Results:

Digestion of HAS

| Time (h) | HAS in $H_2O$ | HAS in citrate buffer |
|---|---|---|
| 0.25 | 6% | 72% |
| 0.5 | 6% | 87% |
| 1 | 9% | — |
| 2 | 9% | 96% |
| 3 | 11% | — |
| 4 | 11% | 97% |
| 5 | — | 97% |
| 6 | — | — |
| 22 | 86% | 99% |

Digestion of HAS+TPS

| Time (h) | HAS + TSP in $H_2O$ | HAS + TSP in citrate buffer |
|---|---|---|
| 0.25 | 5% | 1% |
| 0.5 | — | 26% |
| 1 | 8% | 61% |
| 2 | 6% | 66% |
| 3 | 9% | 66% |
| 4 | 8% | 67% |
| 5 | 11% | 68% |
| 6 | 17% | 68% |
| 22 | 69% | 98% |

Digestion of HAS+TPS+GA 0.1%

| Time (h) | HAS + TSP + GA 0.1% in $H_2O$ | HAS + TSP + GA 0.1% in citrate buffer |
|---|---|---|
| 0.25 | 4% | 39% |
| 0.5 | 4% | 60% |
| 1 | 4% | 65% |
| 2 | 4% | 66% |
| 3 | 3% | 67% |
| 4 | — | 68% |
| 5 | 4% | — |
| 6 | 2% | — |
| 22 | 4% | 98% |

Digestion of HAS+TPS+GA 0.2%

| Time (h) | HAS + TSP + GA 0.2% in $H_2O$ | HAS + TSP + GA 0.2% in citrate buffer |
|---|---|---|
| 0.25 | 5% | 7% |
| 0.5 | 5% | 25% |
| 1 | — | 53% |
| 2 | 5% | 61% |
| 3 | 5% | 63% |
| 4 | 5% | 65% |
| 5 | — | 66% |
| 6 | 5% | — |
| 22 | 5% | — |

Based on the results shown above, the decreases, in percentages, observed for the different compositions are compared below:

in $H_2O$:

| Time (h) | HAS | HAS + TSP | HAS + TSP + GA 0.1% | HAS + TSP + GA 0.2% |
|---|---|---|---|---|
| 0.25 | 6% | 5% | 4% | 5% |
| 0.5 | 6% | — | 4% | 5% |
| 1 | 9% | 8% | 4% | — |
| 2 | 9% | 6% | 4% | 5% |
| 3 | 11% | 9% | 3% | 5% |
| 4 | 11% | 8% | — | 5% |
| 5 | — | 11% | — | — |
| 6 | — | 17% | 4% | 5% |
| 7 | — | — | 2% | 5% |
| 22 | 86% | 69% | 4% | 4% | in citrate buffer:

| Time (h) | HAS | HAS + TSP | HAS + TSP + GA 0.1% | HAS + TSP + GA 0.2% |
|---|---|---|---|---|
| 0.25 | 72% | 1% | 39% | 7% |
| 0.5 | 87% | 26% | 60% | 25% |
| 1 | — | 61% | 65% | 53% |
| 2 | 96% | 66% | 66% | 61% |

-continued

| Time (h) | HAS | HAS + TSP | HAS + TSP + GA 0.1% | HAS + TSP + GA 0.2% |
|---|---|---|---|---|
| 3 | — | 66% | 67% | 63% |
| 4 | 97% | 67% | 68% | 65% |
| 5 | 97% | 68% | — | 66% |
| 6 | — | 68% | — | — |
| 7 | — | — | — | — |
| 22 | 99% | 98% | 98% | 97% |

Digestion of HAS+CMC

| Time (h) | HAS + CMC in H₂O | HAS + CMC in citrate buffer |
|---|---|---|
| 0.25 | 4% | 32% |
| 0.5 | — | 63% |
| 1 | 4% | 77% |
| 2 | 4% | 81% |
| 3 | 7% | 82% |
| 4 | 6% | 83% |
| 5 | — | 84% |
| 6 | 10% | 83% |
| 22 | 12% | 98% |

Digestion of HAS+CMC+GA 0.1%

| Time (h) | HAS + CMC + GA 0.1% in H₂O | HAS + CMC + GA 0.1% in citrate buffer |
|---|---|---|
| 0.25 | 4% | 5% |
| 0.5 | 5% | 42% |
| 1 | 4% | 73% |
| 2 | 5% | 80% |
| 3 | 6% | 82% |
| 4 | 6% | 83% |
| 5 | 5% | 83% |
| 6 | 7% | 83% |
| 22 | 6% | 98% |

Based on the results shown above, the decreases, in percentages, observed for the different compositions are compared below:

in H₂O:

| Time (h) | HAS | HAS + CMC | HAS + CMC + GA 0.1% |
|---|---|---|---|
| 0.25 | 6% | 4% | 4% |
| 0.5 | 6% | — | 5% |
| 1 | 9% | 4% | 4% |
| 2 | 9% | 4% | 5% |
| 3 | 11% | 7% | 6% |
| 4 | 11% | 6% | 6% |
| 5 | — | — | 5% |
| 6 | — | 10% | 7% |
| 7 | 86% | 12% | 6% |
| 22 | 6% | 4% | 4% | in citrate buffer:

| Time (h) | HAS | HAS + TSP | HAS + CMC + GA 0.1% |
|---|---|---|---|
| 0.25 | 72% | 32% | 5% |
| 0.5 | 87% | 63% | 42% |
| 1 | — | 77% | 73% |
| 2 | 96% | 81% | 80% |
| 3 | — | 82% | 82% |
| 4 | 97% | 83% | 83% |
| 5 | 97% | 84% | 83% |
| 6 | — | 83% | 83% |
| 7 | 99% | 98% | 98% |
| 22 | 72% | 32% | 5% |

Digestion of HAS in citrate buffer modified

| Time (h) | HAS in citrate buffer | HAS in citrate buffer modified |
|---|---|---|
| 0.25 | 72% | 1% |
| 0.5 | 87% | 4% |
| 1 | — | 16% |
| 2 | 96% | 32% |
| 3 | — | 43% |
| 4 | 97% | 54% |
| 5 | 97% | 62% |
| 6 | — | 69% |
| 22 | 99% | 97% |

Digestion of HAS+TPS in citrate buffer modified

| Time (h) | HAS + TSP in citrate buffer | HAS + TSP in citrate buffer modified |
|---|---|---|
| 0.25 | 1% | 1% |
| 0.5 | 26% | 2% |
| 1 | 61% | 5% |
| 2 | 66% | 9% |
| 3 | 66% | 15% |
| 4 | 67% | 21% |
| 5 | 68% | 27% |
| 6 | 68% | 32% |
| 22 | 98% | 57% |

Digestion of HAS+TPS+GA 0.1% in citrate buffer modified

| Time (h) | HAS + TSP + GA 0.1% in citrate buffer | HAS + TSP + GA 0.1% in citrate buffer modified |
|---|---|---|
| 0.25 | 39% | 1% |
| 0.5 | 60% | 2% |
| 1 | 65% | 5% |
| 2 | 66% | 9% |
| 3 | 67% | 15% |
| 4 | 68% | 21% |
| 5 | — | 27% |
| 6 | — | 32% |
| 22 | 98% | 57% |

From the data shown above, it was observed that the modification to the concentration of the citrate buffer has a significant decelerating effect on the depolymerization of HAS; in particular, in the HAS+TSP+GA 0.1% formulation, after 22 h, the decrease in molecular weight is just 57%.

Tests were then conducted with different buffers in order to assess the impact on the composition according to the invention.

The following buffers were prepared and used:
Buffer 1: 2.8% mannitol, 0.8% sodium citrate, 0.01% citric acid
Buffer 2: 2.8% mannitol, 0.2% sodium citrate, 0.01% citric acid
Buffer 3: 2.8% mannitol, 0.2% sodium citrate, 0.0025% citric acid Buffer 4: 2.8% mannitol, 0.4% sodium citrate, 0.005% citric acid
Buffer 5: 2.8% mannitol, 0.266% sodium citrate, 0.0033% citric acid

| Buffer | pH | Conductibility in the unaltered state (mS/cm) | Conductibility after dilution 1:10 in water (mS/cm) |
|---|---|---|---|
| 1 | 6.996 | 5.99 | 0.91 |
| 2 | 6.641 | 2.04 | 0.24 |
| 3 | 7.09 | 2.12 | 0.25 |
| 4 | 7.09 | 4.17 | 0.47 |
| 5 | 7.06 | 2.79 | 0.32 |

Compositions were then prepared comprising HAS, TSP, GA formulating them with the different buffers stated above. The results of these tests are shown in the table below:

| | Size | Zp | Conductibility (mS/cm) |
|---|---|---|---|
| Buffer 1 | | | 0.91 |
| +HAS | 51 | −32 | 1.02 |
| +HAS + TSP | 50 | −16 | 1.13 |
| +HAS + TSP + GA 0.05% | 52 | −18 | 1.13 |
| +HAS + TSP + GA 0.1% | 43 | −21 | 1.36 |
| +HAS + TSP + GA 0.2% | 41 | −22 | 1.33 |
| Buffer 2 | | | 0.24 |
| +HAS | ND | −39 | 0.352 |
| +HAS + TSP | 67 | −21 | 0.357 |
| +HAS + TSP + GA 0.05% | 66 | −26 | 0.318 |
| +HAS + TSP + GA 0.1% | 70 | −23 | 0.418 |
| +HAS + TSP + GA 0.2% | 68 | −28 | 0.350 |
| Buffer 3 | | | 0.25 |
| +HAS + TSP + GA 0.1% | 68 | −30 | 0.318 |
| +HAS + TSP + GA 0.2% | 56 | −40 | 0.314 |
| Buffer 4 | | | 0.47 |
| +HAS + TSP + GA 0.1% | 55 | −20 | 0.594 |
| +HAS + TSP + GA 0.2% | 45 | −25 | 0.575 |
| Buffer 5 | | | 0.32 |
| +HAS + TSP + GA 0.1% | 40 | −23 | 0.336 |
| +HAS + TSP + GA 0.2% | 48 | −26 | 0.606 |

It was observed that conductibility increased in the presence of the polysaccharides and the GA, except, in general, when it was present at 0.2%, which appeared, meanwhile, to decrease. Decreasing the sodium acetate, the conductibility decreased while no effects were observed on the citric acid.

The compositions comprising HAS+TSP+GA 0.2% were further examined to assess the mean molecular weight trend over time, in the presence of different buffers:

| | HAS + TSP + GA 0.2% | | | | |
|---|---|---|---|---|---|
| t (sec) | +H₂O | +Buffer 1 | +Buffer 2 | +Buffer 4 | +Buffer 5 |
| | | | % Decrease | | |
| 0.25 | 5 | 7 | 1 | 5 | 2 |
| 0.5 | 5 | 25 | | 1 | 4 |
| 1 | | 53 | 3 | 25 | 9 |
| 2 | 5 | 61 | 6 | 49 | 19 |
| 3 | 5 | 63 | 6 | 57 | 28 |
| 4 | 5 | 65 | 8 | 62 | 35 |
| 5 | | 66 | 7 | 63 | 39 |
| 6 | 5 | | 8 | 63 | 40 |
| 22 | 4 | 97 | 16 | 67 | 47 |

From the data stated above, it was observed that the presence of GA and TSP decelerated depolymerization of HAS by hyaluronidase during the first 6 hours of digestion in citrate buffer; after 22 hours, nevertheless, depolymerization was complete.

The combined effect of GA and TSP in the formulations in water, meanwhile, shielded the action of the hyaluronidase almost entirely, as a result of which no decrease in the molecular weight of HAS was observed.

Depending, therefore, on needs, it is possible to modulate both the pH and the ionic force, and the presence or absence of the buffer, consequently modulating the bioavailability of the GA, in addition to the effect the hyaluronidase has on the HAS.

The invention claimed is:

1. Composition consisting essentially of glycyrrhizin, hyaluronic acid or a salt or a derivative thereof, and a viscosizing agent selected from tamarind seed polysaccharide, polyvinylpyrrolidone, carboxyvinyl polymers, xanthan gum, carboxymethylcellulose, hydroxyethyl cellulose, hydroxypropyl methylcellulose, mucopolysaccharides, cellulose and esters, natural gums and their esters, pectins, polyacrylates, and their mixtures, wherein said derivative of hyaluronic acid is selected from hyaluronic acid esters, self-cross-linked hyaluronic acid esters, succinic acid hemiesters or succinic acid heavy metal salts with hyaluronic acid or with partial or total hyaluronic acid esters, O-sulfated hyaluronic acid, N-sulfated hyaluronic acid and mixtures thereof.

2. The composition of claim 1, wherein said glycyrrhizin is in concentration up to 5.0 wt %, based on the weight of the composition.

3. The composition of claim 1, wherein said hyaluronic acid or a salt or a derivative thereof is in concentration up to 5.0 wt %, based on the weight of the composition.

4. The composition of claim 1, wherein said viscosity agent is in a concentration up to 5.0 wt %, based on the weight of the composition.

5. The composition of claim 1, wherein said viscosizing agent is tamarind seed polysaccharide, carboxymethylcellulose, or a mixture thereof, in a concentration of 0.05-2.0 wt %, based on the weight of the composition.

6. The composition of claim 1, wherein glycyrrhizin and hyaluronic acid or a salt or a derivative thereof are in a weight ratio of 1:1 to 1:20.

7. The composition of claim 1, wherein glycyrrhizin and viscosizing agent are in a weight ratio of 5:1 to 1:15.

8. The composition of claim 1, wherein hyaluronic acid or a salt or a derivative thereof and viscosity agent are in a weight ratio of 1:2 to 10:1.

9. The composition of claim 1, said composition having a pH of 4-7.

10. A composition consisting essentially of
glycyrrhizin,
hyaluronic acid or a salt or a derivative thereof,
a viscosizing agent selected from tamarind seed polysaccharide, polyvinylpyrrolidone, carboxyvinyl polymers, xanthan gum, carboxymethylcellulose, hydroxyethyl cellulose, hydroxypropyl methylcellulose, mucopolysaccharides, cellulose and esters, natural gums and their esters, pectins, polyacrylates, and their mixtures, wherein said derivative of hyaluronic acid is selected from hyaluronic acid esters, self-cross-linked hyaluronic acid esters, succinic acid hemiesters or succinic acid heavy metal salts with hyaluronic acid or with partial or total hyaluronic acid esters, O-sulfated hyaluronic acid, N-sulfated hyaluronic acid and mixtures thereof, and
a buffer, said buffer being selected from citric acid-sodium citrate, acetic acid-sodium acetate, boric-sodium borate acid, citric acid-disodium hydrogen phosphate, citric acid-monopotassium phosphate-boric acid-diethylbarbituric acid, TRIS-borate, and their mixtures.

11. A method of treating ocular affections, said method comprising administering to a subject in need thereof the composition of claim 1, wherein said ocular affection is an inflammatory condition affecting the surface of the eye, selected from dry eye syndrome, Sjögren syndrome, uveitis, conjunctivitis, keratitis, kerato-conjunctivitis, vernal kerato-conjunctivitis, corneal ulcer, atopic keratoconjunctivitis, cicatrizing conjunctivitis, blepharitis, keratitis, lagophthalmos, endophthalmitis, episcleritis and scleritis.

12. An ophthalmic product consisting essentially of glycyrrhizin,
hyaluronic acid or a salt or a derivative thereof,
a viscosizing agent selected from tamarind seed polysaccharide, polyvinylpyrrolidone, carboxyvinyl polymers, xanthan gum, carboxymethylcellulose, hydroxyethyl cellulose, hydroxypropyl methylcellulose, mucopolysaccharides, cellulose and esters, natural gums and their esters, pectins, polyacrylates, and their mixtures, wherein said derivative of hyaluronic acid is selected from hyaluronic acid esters, self-cross-linked hyaluronic acid esters, succinic acid hemiesters or succinic acid heavy metal salts with hyaluronic acid or with partial or total hyaluronic acid esters, O-sulfated hyaluronic acid, N-sulfated hyaluronic acid and mixtures thereof, and
ophthalmologically acceptable excipients.

13. The ophthalmic product of claim 12, said ophthalmic product being a tear substitute, a collyrium, a suspension, an eye spray, a foam, an impregnated wipe, a spray patch, or a combination thereof.

14. The composition of claim 1, wherein said glycyrrhizin is in concentration of 0.05-3.0 wt % based on the weight of the composition.

15. The composition of claim 1, wherein said hyaluronic acid or a salt or a derivative thereof is in concentration of 0.01-3.0 wt % based on the weight of the composition.

16. The composition of claim 1, wherein said viscosity agent is in a concentration of 0.01-3.0 wt % based on the weight of the composition.

17. The composition of claim 1, wherein glycyrrhizin and hyaluronic acid or a salt or a derivative thereof are in a weight ratio of 1:1 to 1:5.

18. The composition of claim 1, wherein glycyrrhizin and viscosizing agent are in a weight ratio of 2:1 to 1:5.

19. The composition of claim 1, wherein hyaluronic acid or a salt or a derivative thereof and viscosity agent are in a weight ratio of 1:1 to 3:1.

20. The composition of claim 1, said composition having a pH of 5.5-6.5.

* * * * *